United States Patent [19]

Karanewsky et al.

[11] Patent Number: 4,474,702
[45] Date of Patent: Oct. 2, 1984

[54] [16,17-A]CYCLOPENTANO PREGNENES

[75] Inventors: Donald S. Karanewsky, East Windsor, N.J.; Christopher M. Cimarusti, Yardley, Pa.

[73] Assignee: E. R. Squibb & Sons, Inc., Princeton, N.J.J

[21] Appl. No.: 572,495

[22] Filed: Jan. 20, 1984

[51] Int. Cl.³ ............................................... C07J 5/00
[52] U.S. Cl. ................................................. 260/397.45
[58] Field of Search .................... 260/397.45; 424/243

[56] References Cited

U.S. PATENT DOCUMENTS 3,944,584  3/1976  Chao et al. .................... 260/397.45
3,979,417  9/1976  Varma et al. .................. 260/397.45
4,213,912  7/1980  Varma ........................... 260/397.45

*Primary Examiner*—Elbert L. Roberts
*Attorney, Agent, or Firm*—Lawrence S. Levinson; Donald J. Barrack

[57] ABSTRACT

Antiinflammatory activity is exhibited by pregnenes having the structural formula

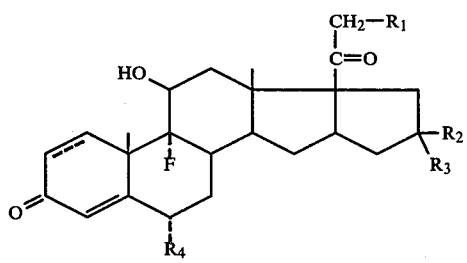

wherein
$R_1$ is hydrogen, hydroxy, halogen, or acyloxy;
$R_2$ and $R_3$ are each hydrogen, $R_2$ and $R_3$ are each methyl, $R_2$ and $R_3$ are each alkylthio, $R_2$ is hydrogen and $R_3$ is alkyl, $R_2$ is hydroxyl and $R_3$ is alkyl, or $R_2$ and $R_3$ taken together are $-(CH_2)_2-$, methylene, or oxo; and
$R_4$ is hydrogen, fluorine, chlorine or bromine.

18 Claims, No Drawings

[16,17a]CYCLOPENTANO PREGNENES

BACKGROUND OF THE INVENTION

U.S. Pat. No. 3,944,584, issued Mar. 16, 1976 discloses pregnenes having the partial structural formula

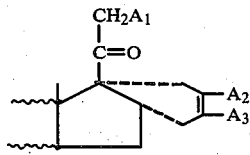

wherein $A_1$ is hydrogen, hydroxy, halogen or acyloxy, and $A_2$ and $A_3$ are the same or different and each is hydrogen, alkyl or aryl. The steroids are said to have antiinflammatory activity.

U.S. Pat. No. 3,979,417 issued Sept. 7, 1976 discloses androstenes having the partial structural formula

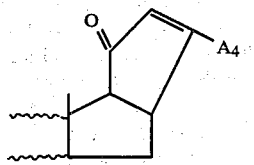

wherein $A_4$ is phenyl, naphthyl, or substituted phenyl or naphthyl. The steroids are said to have antiinflammatory activity.

BRIEF DESCRIPTION OF THE INVENTION

Pregnenes having the formula

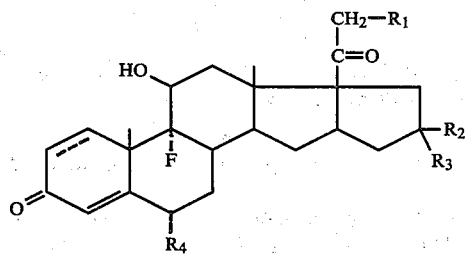

are useful as antiinflammatory agents. In formula I, and throughout the specification, the symbols are as defined below:

$R_1$ is hydrogen, hydroxy, halogen, acyloxy

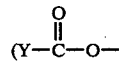

(wherein Y is alkyl or aryl);

$R_2$ and $R_3$ are each hydrogen, $R_2$ and $R_3$ are each methyl, $R_2$ and $R_3$ are each alkylthio, $R_2$ is hydrogen and $R_3$ is alkyl, $R_2$ is hydroxyl and $R_3$ is alkyl, or $R_2$ and $R_3$ taken together are $-(CH_2)_2-$, methylene ($=CH_2$) or oxo ($=O$); and $R_4$ is hydrogen, fluorine, chlorine or bromine.

A dotted line in the 1,2-position of a structural formula in this disclosure indicates the optional presence of ethylenic unsaturation.

The term "aryl", as used throughout the specification, refers to phenyl or phenyl substituted with one, two or three alkyl, alkoxy or halogen groups. The term "halogen", as used throughout the specification, refers to fluorine, chlorine, bromine or iodine.

The terms "alkyl" and "alkoxy", as used throughout the specification refer to groups having 1 to 10 carbon atoms.

DETAILED DESCRIPTION OF THE INVENTION

The steroids of formula I are physiologically active substances which possess gluococortoid and antiinflammatory activity and hence can be used in lieu of known glucocorticoids in the treatment of rheumatoid arthritis, for which purpose they can be administered in the same manner as hydrocortisone, for example, the dosage being adjusted for the relative potency of the particular steroid. In addition, the steroids of this invention can be used topically in lieu of known glucocorticoids in the treatment of skin conditions such as dermatitis, psoriasis, sunburn, neurodermatitis, eczema, and anogenital pruritus.

When given orally, the compounds of this invention may be used in a daily dosage range of 0.1 to 200 milligrams per 70 kilograms, preferably 0.3 to 100 milligrams per 70 kilograms. If administered topically, the compounds of this invention may be used in the range of 0.01 to 5.0% by weight, preferably 0.05 to 2.0% by weight, in a conventional cream or lotion. The topical mode of administration is preferred.

The steroids of formula I can be prepared using as starting materials steroids having the formula

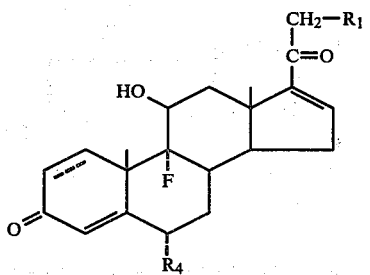

and a compound having the formula

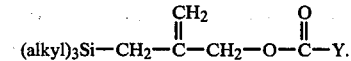

It is desirable to first protect the 11β-hydroxyl group of a steroid of formula II. While many means of protecting the hydroxyl group will be apparent to a person skilled in the steroid art, one particularly desirable method is the acylation of the group. The acylation reaction can be run using an acid anhydride in the presence of a Lewis catalyst, e.g., boron trifluoride etherate, and yields a steroid having the formula

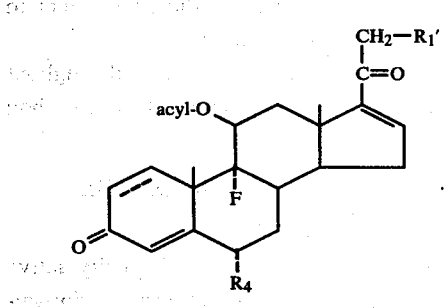

The symbol "$R_1'$" is hydrogen, halogen, or acyloxy. If the starting steroid of formula II contains a 21-hydroxy group, this group will be acylated in addition to the 11β-hydroxy group.

The cycloaddition of a compound of formula III to an enone of formula IV is catalyzed by palladium and proceeds best in the presence of triphenylphosphine. The resulting steroid has the formula

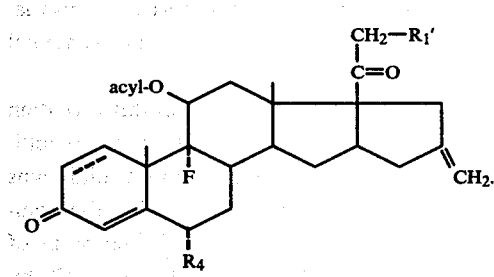

Treatment of a steroid of formula V with base (e.g., lithium hydroxide) deprotects the 11β-hydroxy group and, if $R_1'$ is acyloxy, deacylates the 21-hydroxy group. The resultant steroid has the formula

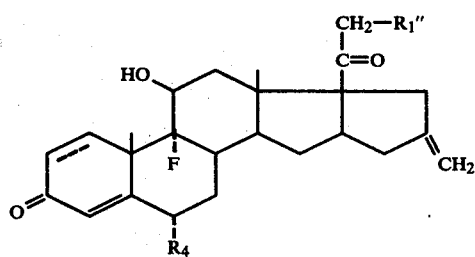

wherein the symbol "$R_1$" is hydrogen, hydroxy or halogen. The 21-esters of formula I can be readily prepared from the steroids of formula VI wherein $R_1''$ is hydroxy using conventional techniques.

Steroids of formula I wherein $R_1$ is hydrogen, acyloxy or halogen and together $R_2$ and $R_3$ are oxo can be prepared by ozonolysis of the corresponding steroid wherein together $R_2$ and $R_3$ are methylene. Those products of formula I wherein $R_1$ is hydroxy and together $R_2$ and $R_3$ are oxo can be prepared by ozonolysis of a corresponding 21-acyloxy steroid wherein together $R_2$ and $R_3$ are methylene. After the ozonolysis the 21-acyloxy product can be deacylated to yield the desired 21-hydroxy steroid.

Steroids of formula I wherein $R_2$ and $R_3$ are each alkylthio can be prepared by treatment of the corresponding steroid of formula I wherein together $R_2$ and $R_3$ are oxo with a thiol such as an alkyl mercaptan in the presence of a Lewis acid catalyst such as boron trifluoride.

Steroids of formula I wherein $R_2$ and $R_3$ are each hydrogen can be prepared by treatment of the corresponding steroid of formula I wherein $R_2$ and $R_3$ are each alkylthio with Raney nickel. The reaction is preferably run in ethanol.

Steroids of formula I wherein $R_2$ is hydroxyl and $R_3$ is alkyl can be prepared by treatment of the corresponding steroid of formula I wherein together $R_2$ and $R_3$ are oxo with an alkyl magnesium halide or an alkyl lithium.

Steroids of formula I wherein $R_2$ is hydrogen and $R_3$ is alkyl can be prepared by treatment of the corresponding steroid of formula I wherein $R_2$ is hydroxyl and $R_3$ is alkyl under dehydrating conditions. Exemplary of the possible dehydration reactions is treatment with methanesulfonyl chloride and triethylamine in dichloromethane followed by catalytic hydrogenation (preferably using tris(triphenylphosphine)rhodium chloride as catalyst) of the resulting mixture of olefins. Alternatively, those steroids of formula I wherein $R_2$ is hydrogen and $R_3$ is methyl can be prepared by catalytic hydrogenation of the corresponding steroid of formula I wherein $R_2$ and $R_3$ are methylene. The preferred catalyst is tris(triphenylphosphine)rhodium chloride.

Steroids of formula I wherein together $R_2$ and $R_3$ are —(CH$_2$)$_2$— can be prepared by treatment of the corresponding steroid of formula I wherein together $R_2$ and $R_3$ are methylene with diiodomethane in the presence of zinc-copper couple.

Steroids of formula I wherein $R_2$ and $R_3$ are each methyl can be prepared by catalytic hydrogenolysis of the corresponding steroid of formula I wherein together $R_2$ and $R_3$ are —(CH$_2$)$_2$—.

The following examples are specific embodiments of this invention.

EXAMPLE 1

(11β,16β)-9-Fluoro-11,21-dihydroxy-4'-methylene-pregna-1,4-dieno[16,17-a]cyclopentane-3,20-dione (A) (11β,16β)-11,21-Di(acetyloxy)-9-fluoro-4'-methylenepregna-1,4-dieno[16,17-a]cyclopentane-3,20-dione A mixture of palladium diacetate (150 mg, 0.67 mmole), triphenyl phosphine (750 mg, 2.86 mmole) and [2-(acetyloxymethyl)-3-allyl]trimethylsilane (135 g, 7.26 mmole) in dry tetrahydrofuran (150 ml) was treated with (11β)-11,21-di(acetyloxy)-9-fluoropregna-1,4,16-triene-3,20-dione (2.22 g, 5.0 mmole) and refluxed under argon. The reaction became homogenous after ca. 20 minutes. After 5.5 hours, the mixture was evaporated to dryness and the residue triturated with ethyl acetate to give 960 mg of recovered starting steroid. The residue on evaporation of the mother liquor was filtered through a pad of silica gel (5 g) eluting with ethyl acetatedichloromethane (1:1). The eluate was evaporated and purified by flash chromatography on silica gel (120 g), eluting with ethyl acetate-hexane (2:3)to give the title compound (710 mg) as white crystals, melting point 204°-205° C. after recrystallization from ethyl acetate-hexane.

(B)
(11β,16β)-9-Fluoro-11,21-dihydroxy-4'-methylene-pregna-1,4-dieno[16,17-a]cyclopentane-3,20-dione A solution of (11β,16β)-11,21-di(acetyloxy)-9-fluoro-4'-methylenepregna-1,4-dieno[16, 17-a]cyclopentane- 3,20-dione (250 mg, 0.50 mmole) in acetonitrile-methanol (2:1, 15.0 ml) was degassed with argon and treated with 1 N lithium hydroxide solution (1.5 ml, 1.5 mmole) and stirred at room temperature under argon for 1.5 hours. The mixture was partitioned between ethyl acetate-5% potassium bisulfate, washed with saturated sodium chloride solution, dried over sodium sulfate and evaporated. The residue was purified by preparative thin-layer chromatography on two 20×20×0.2 cm silica plates eluting with methanol-dichloromethane (5:95) to give 178 mg of the title compound as a white solid. Recrystallization from acetone-hexane gave pure product (142 mg) as white crystals, melting point 210°-212° C.

Anal. Calc'd for $C_{25}H_{31}FO_4$: C, 72.44; H, 7.54; F, 4.58. Found: C, 72.35; H, 7.55; F, 4.70.

EXAMPLE 2

(11β,16β)-21-(Acetyloxy)-9-Fluoro-11-hydroxy4'-methylenepregna-1,4-dieno[16,17-a]cyclopentane-3,20-dione A solution of (11β,16β)-11,21-di(acetyloxy)-9-fluoro-4'-methylenepregna-1,4-dieno[16, 17-a]cyclopentane-3,20-dione (0.750 g, 1.50 mmole, see example 1A) in acetonitrile-methanol (2:1, 45 ml) was degassed with argon, treated with 1 N lithium hydroxide solution and stirred at room temperature under argon for 1.5 hours. The mixture was partitioned between ethyl acetate-5% potassium bisulfate, washed with saturated sodium chloride solution, dried over sodium sulfate and evaporated to give 0.65 g of the corresponding crude 11,21-diol as a white foam. The crude diol (0.64 g) was taken up in acetic anhydride (4.5 ml)-pyridine (3.0 ml) and stirred at room temperature for 45 minutes. The mixture was then treated with 5% potassium bisulfate solution (10 ml), stirred vigorously for ten minutes then extracted with ethyl acetate. The ethyl acetate extract was washed with 5% potassium bisulfate, saturated sodium bicarbonate and saturated sodium chloride, dried over sodium sulfate and evaporated. The crude product was purified by flash chromatography on silica gel eluting with ethyl acetatedichloromethane (1:9) to give the title compound (522 mg) as a white foam. Crystallization from ethyl acetate-hexane gave pure product (460 mg) as white crystals, melting point 187°-188° C.

Analysis Calc'd. for $C_{27}H_{33}FO_5$: C, 71.03; H, 7.29; F, 4.16. Found: C, 70.96; H, 7.25; F, 3.8.

EXAMPLE 3

(11β,16β)-21-(Acetyloxy)-9-fluoro-11-hydroxy-4'-methyl-pregna-1,4-dieno[16,17-a]cyclopentane-3,20-dione A solution of (11β,16β)-21-(acetyloxy)-9-fluoro-11-hydroxy-4'-methylenepregna-1,4-dieno[16.17-a]cyclopentane-3,20-dione (150 mg, 0.33 mole; see example 2) in a mixture of absolute ethanol (7.5 ml)-benzene (7.5 ml) was treated with tris(triphenylphosphine) rhodium chloride (150 mg) and stirred in an atmosphere of hydrogen at room temperature for one hour. The mixture was then evaporated to dryness and the residue filtered through a pad of neutral alumina (Activity II, 2-3 g) eluting with acetone-hexane (35:65). The yellow residue obtained on evaporation of the eluate was purified first by preparative thin-layer chromatography on two 20×20×0.2 cm silica gel plates eluting with ethyl acetate-dichloromethane (1:1) and finally by flash chromatography on silica (25 g) eluting with acetone-hexane (1:3) to give the title compound (127 mg) as a white foam. Crystallization from ethyl acetate-hexane gave the title compound (113 mg) as white crystals. Recrystallization from the same solvents gave analytically pure product (97 mg) as white crystals, melting point 179°-192° C.

Anal. Calc'd. for $C_{27}H_{35}FO_5$: C, 70.72; H, 7.69; F, 4.14. Found: C, 70.64; H, 7.91; F, 4.10.

EXAMPLE 4

(11β,16β)-21-(Acetyloxy)-9-fluoro-11-hydroxypregna-1,4-dieno[16,17-a]cyclopentane-3,4',20-trione A solution of (11β,16β)-21-(acetyloxy)-9-fluoro-11-hydroxy-4'-methylenepregna-1,4-dieno[16,17-a]cyclopentane-3,20-dione (175 mg, 0.38 mmole; see example 2) in a mixture of dichloromethane (10 ml) and methanol (10 ml) at −78° C. (dry ice-acetone bath) was treated with ozone until the pale blue color of excess ozone appeared. The excess ozone was immediately discharged by passing a stream of dry nitrogen through the solution and excess dimethylsulfide (0.5 ml) was added. After stirring at −78° C. for thirty minutes, at 0° C. for thirty minutes and at room temperature for thirty minutes, the mixture was evaporated to dryness. The crude product was purified by preparative thin-layer chromatography on two 20×20×0.2 cm silica gel plates eluting with acetone-dichloromethane (1:3) to give the title compound (123 mg) as a white crystalline solid. Recrystallization from acetone-hexane gave pure product (101 mg) as fluffy white crystals, melting point 314°-315° C. (dec.).

Anal. Calc'd. for $C_{26}H_{31}FO_6$: C, 68.11; H, 6.82; F, 4.14. Found: C, 67.87; H, 6.89; F, 4.13.

EXAMPLE 5

(11β,16β)-9-Fluoro-11,21-dihydroxy-4'-methylpregna-1,4-dieno[16,17-a]cyclopentane-3,20-dione (A)

(11β,16β)-11,21-Di(Acetyloxy)-9-fluoro-4'-methyl-pregna-1,4-dieno[16,17-a]cyclopentane-3,20-dione A suspension of freshly prepared tris(triphenylphosphine) rhodium chloride (0.30 g) in a solution of (11β,16β)-11,21-di(acetyloxy)-9-fluoro-4'-methylenepregna-1,4-dieno[16,17-a]cyclopentane-3,20-dione (298 mg, 0.50 mmole; see example 1A) in absolute ethanol (20 ml)-benzene (20 ml) was stirred under an atmosphere of hydrogen for 45 minutes. The mixture was evaporated to dryness, the residue taken up in dichloromethane and filtered through a pad of neutral alumina eluting with ethyl acetate-dichloromethane (1:1). Evaporation of the eluate and purification by flash chromatography on silica gel (45 g) gave the title compound (249 mg), melting point 236°-238° C. after recrystallization from ethyl acetate-hexane.

(B)

(11β,16β)-9-Fluoro-11,21-dihydroxy-4'-methylpregna-1,4-dieno[16,17-a]cyclopentane-3,20-dione A solution of (11β,16β)-11,21-di(acetyloxy)-9-fluoro-4'-methylpregna-1,4-dieno[16,17-a]cyclopentane-3,20-dione (238 mg, 0.475 mmole) in acetonitrile (10.0 ml) methanol (5.0 ml) was degassed with argon and treated with 1 N lithium hydroxide solution (1.2 ml, 1.2 mmole) and stirred at room temperature under argon for 2 hours. The mixture was partitioned between ethyl acetate-5% potassium bisulfate, the organic phase washed with saturated sodium chloride solution, dried over sodium sulfate and evaporated. The crude product was purified by preparative thin-layer chromatography on two 20×20×0.2 cm silica plates, eluting with methanol-dichloromethane (5:95) to give 166 mg of the title steroid as a white solid. Recrystallization from acetone-hexane gave pure product (144 mg) as off-white crystals, melting point 232°–236° C.

Anal. Calc'd for $C_{25}H_{35}O_4F$: C, 72.09; H, 7.99; F, 4.56. Found: C, 71.93; H, 8.10; F, 4.5.

What is claimed is:

1. A steroid having the formula

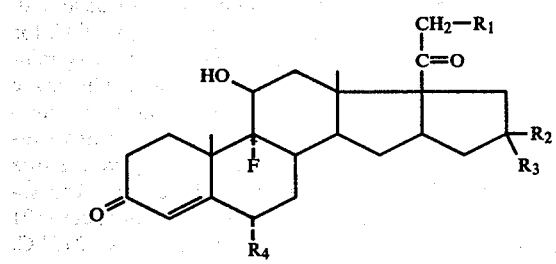

or a 1,2-dehydro derivative thereof, wherein $R_1$ is hydrogen, hydroxy, halogen or

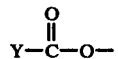

wherein Y is alkyl or aryl;

$R_2$ and $R_3$ are each hydrogen, $R_2$ and $R_3$ are each methyl, $R_2$ and $R_3$ are each alkylthio, $R_2$ is hydrogen and $R_3$ is alkyl, $R_2$ is hydroxyl and $R_3$ is alkyl, or $R_2$ and $R_3$ taken together are —(CH$_2$)$_2$—, methylene, or oxo; and $R_4$ is hydrogen, fluorine, chlorine or bromine.

2. A steroid in accordance with claim 1 having the formula

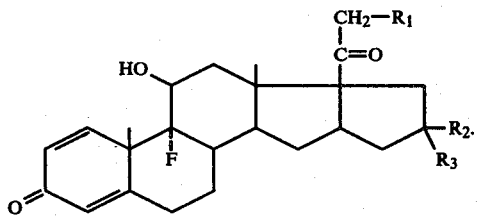

3. A steroid in accordance with claim 2 wherein $R_1$ is hydrogen.

4. A steroid in accordance with claim 2 wherein $R_1$ is hydroxy.

5. A steroid in accordance with claim 2 wherein $R_1$ is halogen.

6. A steroid in accordance with claim 2 wherein $R_1$ is

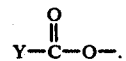

7. A steroid in accordance with claim 6 wherein Y is methyl.

8. A steroid in accordance with claim 2 wherein together $R_2$ and $R_3$ are methylene.

9. A steroid in accordance with claim 2 wherein together $R_2$ and $R_3$ are oxo.

10. A steroid in accordance with claim 2 wherein $R_2$ is hydrogen and $R_3$ is methyl.

11. A steroid in accordance with claim 8 wherein $R_1$ is hydroxy or acetyloxy.

12. A steroid in accordance with claim 9 wherein $R_1$ is hydroxy or acetyloxy.

13. A steroid in accordance with claim 10 wherein $R_1$ is hydroxy or acetyloxy.

14. The steroid in accordance with claim 2, (11β,16β)-9-fluoro-11,21-dihydroxy-4'-methylenepregna-1,4-dieno[16,17-a]cyclopentane-3,20-dione.

15. The steroid in accordance with claim 2, (11β,16β)-21-(acetyloxy)-9-fluoro-11-hydroxy-4'-methylenepregna-1,4-dieno[16,17-a]cyclopentane-3,20-dione.

16. The steroid in accordance with claim 2, (11β,16β)-(21-acetyloxy)-9-fluoro-11-hydroxy-4'-methylpregna-1,4-dieno[16,17-a]cyclopentane-3,20-dione.

17. The steroid in accordance with claim 2, (11β,16β)-21-(acetyloxy)-9-fluoro-11-hydroxypregna-1,4-dieno[16,17-a]cyclopentane-3,4',20-trione.

18. The steroid in accordance with claim 2, (11β,16β)-9-fluoro-11,21-dihydroxy-4'-methylpregna-1,4-dieno[16,17-a]cyclopentane-3,20-dione.

* * * * *